US00PP08053P

United States Patent [19]

Hofmann

[11] Patent Number: Plant 8,053

[45] Date of Patent: Dec. 1, 1992

[54] VARIETY OF GERANIUM NAMED SASSY DARK RED

[75] Inventor: Christa Hofmann, Dresden, Fed. Rep. of Germany

[73] Assignee: Oglevee, Ltd., Connellsville, Pa.

[21] Appl. No.: 690,043

[22] Filed: Apr. 23, 1991

[51] Int. Cl.[5] ..... A01H 5/00

[52] U.S. Cl. ..... Plt./87.12

[58] Field of Search ..... Plt./68, 87.12

*Primary Examiner*—Howard J. Locker

*Attorney, Agent, or Firm*—Webb, Burden, Ziesenheim & Webb

[57] ABSTRACT

This new cultivar has a very compact and uniform plant habit in which the deep red flowers are positioned appropriately above the foliage. Further, the variety does exceptionally well when grown indoors and response time can be shortened by up to two weeks in blooming time. Cutting production and ease of rooting have also been improved.

1 Drawing Sheet

BACKGROUND OF THE INVENTION

The present invention comprises a new and distinct cultivar of *Pelargonium*×*hortorum* known by the varietal name Sassy Dark Red (V.E.B. Number P-3 Oglevee Code 7026). The new variety was discovered in a selected breeding program in 1985 in Berlin, East Germany. The new variety is a selection from the crossing of PAC Cherry and purple colored breeding stocks. The new variety was first asexually reproduced by cuttings at VEB Saat-und Pflanzgut, Ex-und Import, Moosdorfstrasse 3, 1193 Berlin, East Germany. The new variety has been asexually reproduced by cuttings at Oglevee Ltd. in Connellsville, Pa. over a several year period. It has also been trial and field tested at Connellsville and has been found to retain its distinctive characteristics through successive propagations.

The cultivar when grown in a glass greenhouse in Connellsville, Pa. using natural light and 60° F. night, 68° F. day and 71° F. vent, has a response time of six weeks from a rooted cutting to flowering in a 10 cm. pot. The response time was determined on plants grown in soilless media employing constant fertilizer 200 parts per million of nitrogen and potassium in full light. The rooted cuttings were potted Feb. 14, 1990 and flowered on Apr. 1, 1990.

DESCRIPTION OF THE DRAWING

The accompanying photographic drawing illustrates the new cultivar, with the colors shown being as nearly true as possible with color illustrations of this type.

DESCRIPTION OF THE NEW PLANT

The following detailed description sets forth the characteristics of the new cultivar. The data which defines these characteristics were collected by asexual reproductions carried out by Oglevee Ltd. in Connellsville, Pa. The plant history was taken on six week plants blossomed under natural light in a greenhouse and the color readings were taken indoors under 100–125 foot candles of florescent cool white light. Color references are primarily to the RHS Colour Chart of the Royal Horticultural Society of London.

THE PLANT

Classification:

*Botanical.*—*Pelargonium*×*hortorum.*

*Commercial.*—Zonal Geranium.

Form: Upright, compact habit, basal branching.

*Height.*—16 to 17 cm. from media surface.

*Growth.*—Free and early flowering, compact mound habit, free branching from the base.

Strength: Very sturdy; stands upright without artificial support.

Foliage: Little or no zoning present; stalked leaf attachment.

Leaves:

*Size.*—7.0 to 8.5 cm. across at widest point. Shape: Reniform; cordate base. Margin: Crenate. Texture: Slightly pubescent; slightly reflective.

*Color.*—Top: Green group 137B. Bottom: Green group 137C.

*Ribs and veins.*—Palmate venation. Color: Yellow/green group 146D.

Petioles:

*Color.*—Yellow/green group 146B.

*Length.*—5.5 to 10.0 cm.

Stem:

*Color.*—Yellow/green group 146C.

*Internodes.*—1.5 to 2.0 cm. in length.

THE BUD

Shape: Upright; hemispherical cluster.

Size: 1.5 to 3.0 cm. across.

INFLORESCENCE

Blooming habit: Continuous; upright; semi-double hemispherical bloom.

Size: 8.0 to 9.5 cm. across.

Borne: Umbel; florets on pedicel, pedicel on peduncle; 7.0 to 10.0 cm. above foliage.

Florets:

*Form.*—Flat to slightly cupped.

*Color.*—Top: Red group 45C with an eye of Red group 43C on upper petals. Bottom: Red group 45D.

*Petals.*—Obovate; separate, not united; margin entire; smooth, flat to slightly cupped; 6 to 8 in number.

*Size.*—4.0 to 5.0 cm. across.

*Texture and appearance.*—Smooth; color from a distance appears a deep red, almost fluorescent.

Petaloids:

*Quantity.*—Varies from none to 3.

*Shape.*—Elongated, twisted.

*Color.*—Red group 45C.

Pedicel:

*Length.*—2.0 to 2.5 cm. in length.

*Color.*—Greyed/purple group 183C at floret end and bends to Yellow/green group 146C.

Peduncle: Arises from the node opposite leaf petiole.

*Color.*—Yellow/green group 146B.

*Length.*—17.0 to 18.5 cm.

Disease resistance: Not known.

Lasting quality: This variety has proven to do well indoors and outdoors during testing the past two years. The plant holds its compact shape and continues to bloom.

REPRODUCTIVE ORGANS

Stamens:

*Anthers.*—2.0 to 3.0 mm. in length.

*Filaments.*—White at base to Red group 44C at tip; flat and irregular in shape; 6 to 8 mm. in length.

*Pollen.*—Golden brown.

Pistils:

*Number.*—One.

*Length.*—8.0 to 9.0 mm.

*Stigma.*—One; 5 or 6 parted; red-purple in color.

*Style.*—Red-purple in color; 2.0 to 3.0 mm. in length.

Ovaries: Superior; pale green in color; very pubescent; 5.0 to 6.0 mm. in length; 2.0 to 3.0 mm. across.

Fruit: None observed.

GENERAL CHARACTERISTICS

Sassy Dark Red has been trialed outdoors during the summers of 1988 and 1989 against Sunbelt Dark Red. The two are very similar in color but the plant habit of Sassy Dark Red is more compact and uniform than Sunbelt Dark Red. The flowers of Sassy Dark Red are also positioned more appropriately above the foliage.

Indoor performance is also quite exceptional. When grown in a 4" pot for the spring market, this new variety can be up to two weeks earlier in blooming time. Cutting production and ease of rooting have also been improved.

I claim:

1. A new and distinct variety of Geranium plant substantially as shown and described.

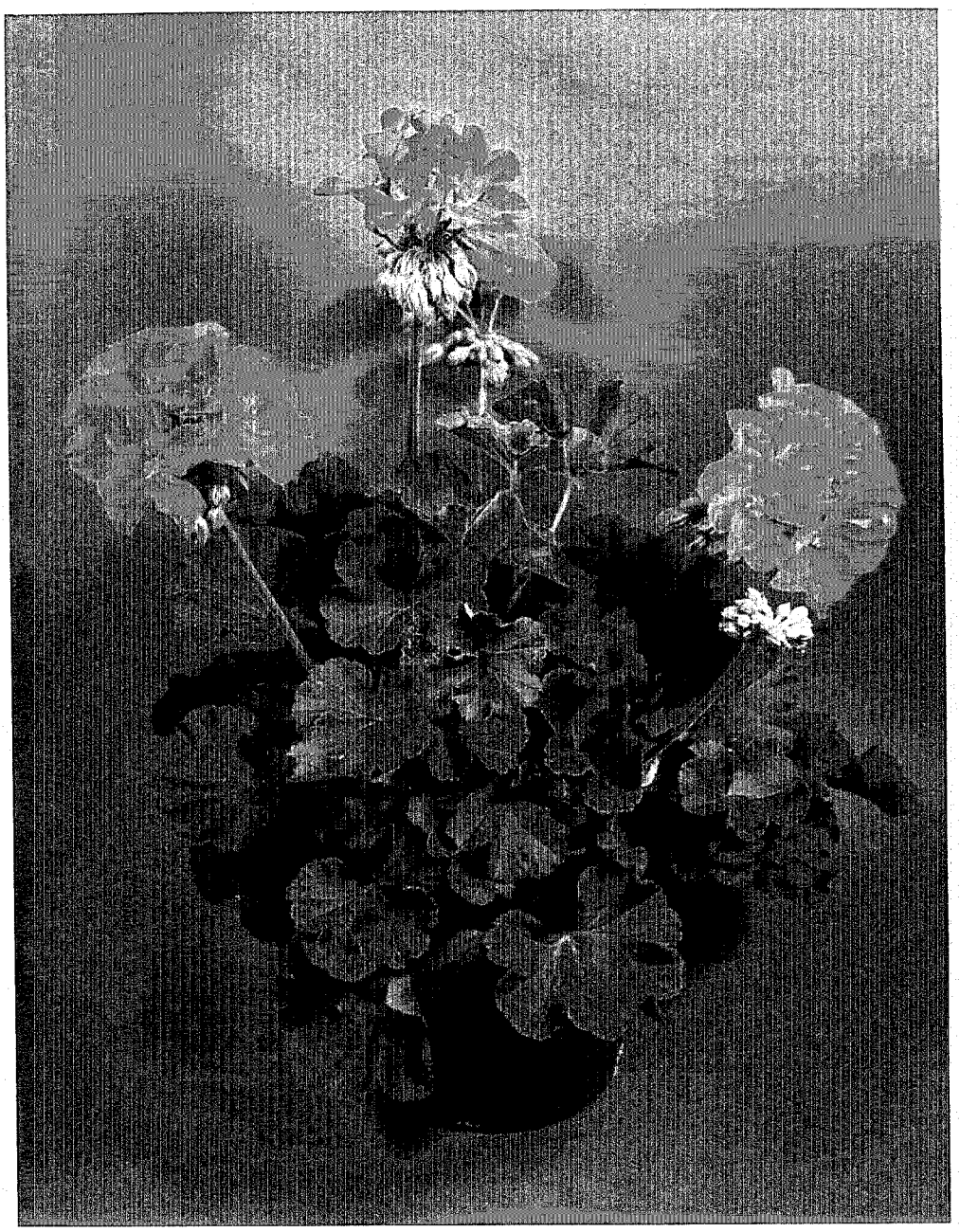

* * * * *